(12) United States Patent
Cistola et al.

(10) Patent No.: US 12,303,247 B2
(45) Date of Patent: May 20, 2025

(54) METHODS AND TOOLS FOR DIAGNOSING INSULIN RESISTANCE AND ASSESSING HEALTH STATUS USING NMR RELAXATION TIMES FOR WATER

(71) Applicant: UNIVERSITY OF NORTH TEXAS HEALTH SCIENCE CENTER AT FORT WORTH, Fort Worth, TX (US)

(72) Inventors: David P. Cistola, El Paso, TX (US); Michelle D. Robinson, Dallas, TX (US)

(73) Assignee: University of North Texas Health Science Center at Fort Worth, Fort Worth, TX (US)

( * ) Notice: Subject to any disclaimer, the term of this patent is extended or adjusted under 35 U.S.C. 154(b) by 668 days.

(21) Appl. No.: 17/509,099

(22) Filed: Oct. 25, 2021

(65) Prior Publication Data

US 2022/0039680 A1 Feb. 10, 2022

Related U.S. Application Data

(63) Continuation of application No. 15/548,442, filed as application No. PCT/US2016/016906 on Feb. 6, 2016, now abandoned.
(Continued)

(51) Int. Cl.
*A61B 5/055* (2006.01)
*A61B 5/00* (2006.01)
(Continued)

(52) U.S. Cl.
CPC .......... *A61B 5/055* (2013.01); *A61B 5/14532* (2013.01); *A61B 5/4866* (2013.01);
(Continued)

(58) Field of Classification Search
None
See application file for complete search history.

(56) References Cited

U.S. PATENT DOCUMENTS

| 4,701,708 A | 10/1987 | Hardy et al. |
| 5,327,088 A | 7/1994 | Pipe |

(Continued)

FOREIGN PATENT DOCUMENTS

| WO | WO 2014/071411 | 5/2014 |
| WO | WO 2014/169229 | * 10/2014 |
| WO | WO 2014/190071 | 11/2014 |

OTHER PUBLICATIONS

NMR Relaxation Times T1 and T2 of Water in Plasma from Patients with Lung Carcinoma: Correlation of T2 with Blood Sedimentation Rate.*

(Continued)

*Primary Examiner* — Shahdeep Mohammed
(74) *Attorney, Agent, or Firm* — SALIWANCHIK, LLOYD & EISENSCHENK

(57) ABSTRACT

The subject invention pertains to a method that involves at least three steps: (1) acquisition of a NMR data set or spin relaxation curve for plasma, serum or whole blood samples, (2) analysis of the NMR data or relaxation curve to extract the $T_2$ relaxation times for water (or surrogates thereof), and (3) conversion of the water $T_2$ (or surrogates thereof) into a measure of someone's health status (referred to as a $T_2$ health score depending on the $T_2$ value associated with the score). The $T_2$ health score utilizes a statistical database derived from previous studies of subjects of normal, healthy individuals to those having varying degrees of hidden or subclinical metabolic abnormalities, such as inflammation, insulin resistance, lipid abnormalities (dyslipidemia), oxi- (Continued)

dative stress or other abnormalities, and provides a measure of a subject's overall health status.

20 Claims, 6 Drawing Sheets

Related U.S. Application Data

(60) Provisional application No. 62/155,852, filed on May 1, 2015, provisional application No. 62/113,112, filed on Feb. 6, 2015.

(51) Int. Cl.
*A61B 5/145* (2006.01)
*G01N 24/08* (2006.01)
*G01R 33/44* (2006.01)
*G16H 50/30* (2018.01)

(52) U.S. Cl.
CPC ........... *G01N 24/08* (2013.01); *G01R 33/448* (2013.01); *G16H 50/30* (2018.01); *A61B 5/145* (2013.01)

(56) References Cited

U.S. PATENT DOCUMENTS

| | | |
|---|---|---|
| 2003/0108485 A1 | 6/2003 | Bolam et al. |
| 2006/0111846 A1 | 5/2006 | Szyperski et al. |
| 2006/0164084 A1 | 7/2006 | Lomnes |
| 2010/0225316 A1 | 9/2010 | Jacob et al. |
| 2011/0160563 A1 | 6/2011 | Glogau et al. |
| 2012/0029340 A1* | 2/2012 | Does .................... G01R 33/448 600/410 |
| 2014/0212901 A1* | 7/2014 | Lowery, Jr. .......... A61B 5/0263 435/13 |
| 2014/0273247 A1 | 9/2014 | Cistola et al. |
| 2016/0047761 A1* | 2/2016 | Yu .......................... G01R 33/50 324/309 |

OTHER PUBLICATIONS

Written Opinion in International Application No. PCT/US2016/016906, Jun. 10, 2016, pp. 1-6.
Schuhmacher, J. H. et al. "NMR Relaxation Times $T_1$ and $T_2$ of Water in Plamsa from Patients with Lung Carcinoma: Correlation of $T_2$ with Blood Sedimentation Rate" *Magnetic Resonance in Medicine*, 1987, pp. 537-547, vol. 5.
Keeling, S.L. et al. "Deconvolution for DCE-MRI Using an Exponential Approximation Basis" *Med Image Anal*, Feb. 2009, pp. 80-0-, vol. 13, No. 1.
Haacke, E. M. et al. "T2 Deconvolution in MR Imaging and NMR Spectroscopy" *Journal of Magnetic Resonance*, Feb. 1988, pp. 440-457, vol. 76, No. 3.
Weisman, S. M. et al. "Evaluation of the Benefits and Risks of Low-Dose Aspirin in the Secondary Prevention of Cardiovascular and Cerebrovascular Events" *Arch Intern Med.*, Oct. 28, 2002, pp. 2197-2202, vol. 162.

* cited by examiner

METHODS AND TOOLS FOR DIAGNOSING INSULIN RESISTANCE AND ASSESSING HEALTH STATUS USING NMR RELAXATION TIMES FOR WATER

CROSS-REFERENCE TO RELATED APPLICATIONS

This application is a continuation of U.S. application Ser. No. 15/548,442, filed Aug. 3, 2017, which is the U.S. national stage application of International Patent Application No. PCT/US2016/016906, filed Feb. 6, 2016, which claims the benefit of U.S. Provisional Application Ser. No. 62/113,112, filed Feb. 6, 2015, and 62/155,852, filed May 1, 2015, the disclosures of which are hereby incorporated by reference in their entirety, including all figures, tables and amino acid or nucleic acid sequences.

BACKGROUND OF THE INVENTION

Conventional proteomics uses mass spectrometry to measure a large number of protein biomarkers to establish profiles of health and disease (1). The subject application monitors changes in blood protein profiles by measuring just one biomarker: water $T_2$. Conventional proteomics focuses on the less abundant proteins in blood or body fluids after removing the most abundant ones during pre-treatment prior to analysis (2, 3). In contrast, the subject application has developed a technique, termed "inverse proteomics" that involves no pre-treatment or sample manipulation and leverages the information content of all blood proteins and lipoproteins, including the most abundant ones.

BRIEF SUMMARY OF THE INVENTION

This application provides a means for developing an inexpensive blood test for front-line health screening and monitoring. Also, this test can be used for the diagnosis of insulin resistance syndrome, an early metabolic abnormality that leads to type 2 diabetes. The test analyzes the spin relaxation times ($T_2$ and/or $T_1$ or surrogates of $T_2$ and/or $T_1$) of water in plasma, serum or whole blood using nuclear magnetic resonance (NMR). The blood samples can be obtained using a conventional needle stick or finger prick. However, given the intensity of the water NMR signal, it should be feasible to monitor the relaxation times of water in blood from outside of the body using a NMR-enabled finger probe, earlobe clip or a wristwatch-like device linked to a smart phone. Portable NMR devices are already available (1). The NMR $T_2$ (or surrogates thereof) for water reports on the concentration and chemical state of the proteins and lipoproteins in the blood. We refer to this approach as inverse proteomics.

The subject application has determined that lower water $T_2$ and/or $T_1$ values (or surrogate values for $T_2$ and/or $T_1$) in serum and plasma are indicative of increasing degrees of metabolic dysfunction, even in an essentially healthy population with clinical lab values that fall in the normal reference ranges. The unique value of time-domain nuclear magnetic resonance (TD-NMR) is that an individual's overall health status with respect to insulin resistance, inflammation, dyslipidemia and acid-base abnormalities can be assessed simultaneously in one measurement without having to survey a large panel of clinical lab tests or biomarkers, which is expensive and impractical. Given its simplicity, water $T_2$ and/or $T_1$ (4), or surrogates of $T_2$ and/or $T_1$, can serve as a screening tool for the early identification of individuals with hidden risk for diseases that are linked with metabolic abnormalities. Non-limiting examples of such diseases include, but are not limited to, diabetes, coronary artery disease, and Alzheimer's disease (5, 6). These disorders account for much of the morbidity and mortality in modern societies. There is a continuing need for effective screening tools that can be implemented practically, inexpensively and broadly across the population. Such tools will have a place in P4 medicine: personal, predictive, preventative and participatory medicine (7). The invention disclosed herein provides a solution to this continuing need.

BRIEF DESCRIPTION OF THE TABLES

Figure 1:
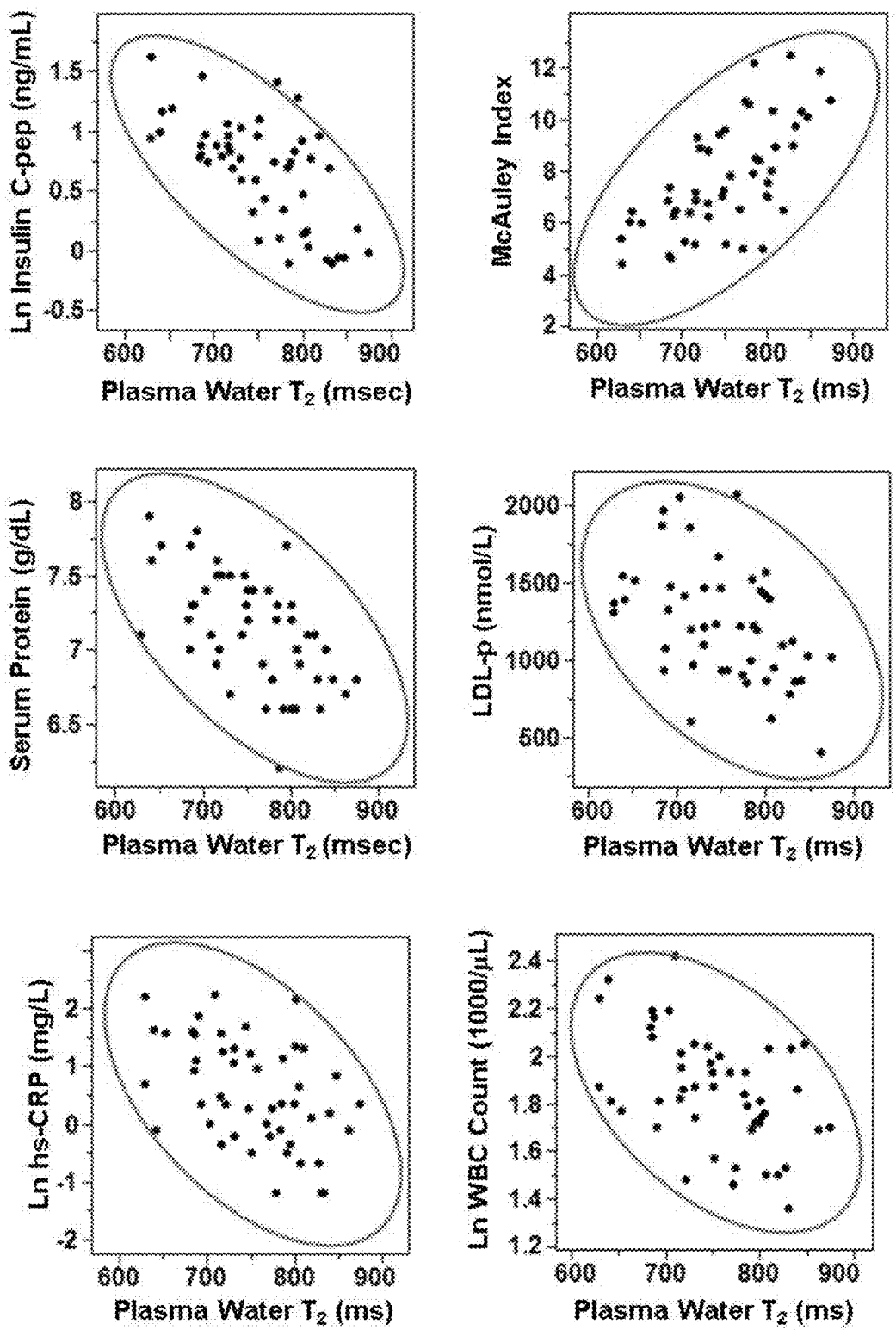
FIG. 1 displays scatterplots for the bivariate correlations between plasma water $T_2$ values and diagnostic markers for the human subjects enrolled in this study. Each black circle represents a data point for an individual human subject enrolled in this study. Values are enclosed in a density ellipse calculated from the bivariate normal distribution fit to the X and Y variables at the 95% confidence level. It provides a graphical indication of the correlation between the variables. upper left: plasma water $T_2$ vs. ln insulin C-peptide; upper right: plasma water $T_2$ vs. the McAuley Index for insulin sensitivity; middle left: plasma water $T_2$ vs. total serum protein concentration; middle right: plasma water $T_2$ vs. LDL particle number; lower left: serum water $T_2$ vs. hs-CRP; lower right: serum water $T_2$ vs. ln white blood cell count.

Table 1: Characteristics of the Human Study Group, n=51.
Table 2: Biomarkers Measured in this Study.
Table 3: Bivariate correlation coefficients for plasma water $T_2$ with markers of insulin sensitivity and glucose tolerance (A), protein concentration and viscosity (B), inflammation (C), and cholesterol metabolism (D).
Table 4: Single and Multiple Regression Models for Plasma Water $T_2$.
Table 5: Mean plasma water $T_2$ values for conditions and measures associated with early insulin resistance syndrome.
Table 6: Sensitivity, specificity and area-under-the-curve (AUC) parameters indicating the ability of various measures to diagnose insulin resistance (as defined by the McAuley Index) in normoglycemic subjects, n=46.

DETAILED DISCLOSURE OF THE INVENTION

The term "about" is used in this patent application to describe some quantitative aspects of the invention, for example, time. It should be understood that absolute accuracy is not required with respect to those aspects for the invention to operate. When the term "about" is used to describe a quantitative aspect of the invention, the relevant aspect may be varied by up to ±10%. As used herein, the term "subject" refers to a human or non-human animal, such as a rat, mouse, pig, dog, cat, horse or any other animal, including animal models of human diseases.

For the purposes of this invention, $T_2$ refers to the NMR spin-spin relaxation time constant. Surrogate measures that approximate $T_2$, such as $T_2^*$ (the decay time constant from a free induction decay curve), or LW, the linewidth of a peak from a Fourier transformed NMR spectra, or any other representation of the NMR data that permits inferences or estimates of the $T_2$ relaxation rate can be used as alternative surrogates for $T_2$. Likewise, $T_1$ refers to the spin-lattice relaxation time constant. However, any surrogate measures that permit one to estimate or make inferences about $T_1$ can also be used as a surrogate for $T_1$ values. Where the terms "$T_2$ and/or $T_1$ data" or "$T_2$ and/or $T_1$ values" are used, it should be understood that surrogate measures can be substituted for these terms.

The subject application discloses a method that involves at least three steps: (1) acquisition of a NMR relaxation decay or recovery curve for plasma, serum or whole blood samples, or for tissues monitored from outside the body, (2) analysis of the relaxation decay or recovery curve to extract the $T_2$ and/or $T_1$ relaxation times (or $T_2$ or $T_1$ surrogates) for water, and (3) conversion of the water $T_2$ and/or $T_1$ values (or surrogate values therefor) into a measure of someone's health status (referred to as a $T_2$ or $T_1$ health score depending on the value associated with the score). The $T_1$ and/or $T_2$ health score utilizes a statistical database derived from previous studies of subjects having varying degrees of metabolic abnormalities, such as inflammation, insulin resistance, lipid abnormalities (dyslipidemia), oxidative stress, brain abnormalities or other disorders, and provides a measure of a subject's overall metabolic and brain health status. Specifically, the disclosed method detects or rules out hidden problems such as inflammation, insulin resistance, lipid abnormalities (dyslipidemia), oxidative stress, brain abnormalities or other disorders. In other words, the disclosed method identifies metabolic abnormalities that are subclinical (hidden) by conventional diagnostic criteria (i.e., undiagnosed metabolic abnormalities or metabolic abnormalities having no recognizable signs or symptoms that would permit for the diagnosis of a given metabolic abnormality). The disclosed invention has value as a front-line health screening test and provides a subject with a $T_2$ and/or $T_1$ Health Score that provides individuals with an overall assessment of their metabolic and brain health. The $T_2$ and/or $T_1$ Health Score provides evidence of hidden (undiagnosed) abnormalities that could lead to disease in the future. Non-limiting examples of these abnormalities include, but are not limited to, inflammation, insulin resistance, neurological abnormalities, oxidative stress and lipid abnormalities. Early detection and subsequent intervention can remedy or delay the manifestation of disease arising from the abnormalities disclosed herein (e.g., atherosclerosis, etc.) Thus, if an apparently healthy subject has a moderately low $T_2$ and/or $T_1$ Health Score, the subject can choose an intervention, such as an exercise program, and check the score 4-8 weeks later to see if the health score has improved. Alternatively, the subject can alter its diet, take low dose aspirin or add a nutritional supplement, such as an antioxidant or a fish oil and assess the impact of this change in diet on the $T_2$ and/or $T_1$ Health Score. Subjects with the lowest scores would be advised to visit their physician for a more complete workup to rule out a disease diagnosis and/or subjects can be treated with an appropriate therapeutic intervention. With respect to the overall assessment of metabolic and brain health, subjects can be separated into at least three categories. In some embodiments, the subjects can be separated as follows on the basis of the $T_2$ and/or $T_1$ Health Score (based on plasma $T_2$ values): >800: lowest likelihood of metabolic abnormalities; 700-800 or between 720 to 800: medium likelihood of metabolic abnormalities; <700 or <720: highest likelihood of metabolic abnormalities, including early insulin resistance syndrome. Thus, subjects with a $T_2$ and/or $T_1$ Health Score of 800 or less can be treated according to the methods disclosed herein, subjected to heightened monitoring for the development of metabolic abnormalities or referred to a health provider for further evaluation for a hidden metabolic abnormality, such as inflammation, insulin resistance, lipid abnormalities (dyslipidemia), oxidative stress, brain abnormalities or other disorders.

As discussed above, the subject application has determined that lower water $T_2$ and/or $T_1$ values (or surrogate values $T_2$ and/or $T_1$) in serum and plasma are indicative of increasing degrees of metabolic dysfunction, even in an essentially healthy population with clinical lab values that fall in the normal reference ranges. The unique value of TD-NMR is that an individual's overall health status with respect to insulin resistance, inflammation, dyslipidemia and possibly oxidative stress can be assessed simultaneously in one measurement without having to survey a large panel of clinical lab tests or biomarkers. Given its simplicity, water $T_2$ and/or $T_1$ (4) (or surrogate values therefor) can serve as a screening tool for the early identification of individuals with hidden risk for diseases that are linked with metabolic abnormalities. Non-limiting examples of such diseases include, but are not limited to, diabetes, coronary artery disease, and Alzheimer's disease (5, 6). These disorders account for much of the morbidity and mortality in modern societies. There is a continuing need for effective screening tools that can be implemented practically, inexpensively and broadly across the population will have a place in P4 medicine: personal, predictive, preventative and participatory (7). The invention disclosed herein provides a solution to this continuing need. This subject application describes methods for determining an individual's overall health status with respect to insulin resistance, inflammation, dyslipidemia, oxidative stress and brain abnormalities can be assessed simultaneously in one measurement without having to survey a large panel of clinical lab tests or biomarkers by measuring water $T_2$ and/or $T_1$ values (or surrogate values therefor) in samples obtained from a subject. In various embodiments, the samples are subjected to no pre-treatment or other sample manipulation. The method leverages the information content of all plasma and serum proteins, including the most abundant ones, in developing $T_2$ and/or $T_1$ Health Scores.

In one aspect, the method includes the of placing a small volume of a sample comprising water into a NMR instrument tuned to measure a particular nucleus, such as $^1H$, $^2H$ or $^{17}O$, by applying a series of radiofrequency pulses with intermittent delays in order to measure spin-spin ("$T_2$") and/or spin-lattice ("$T_1$") relaxation time constants from the time-domain decay or recovery of the signal. In other embodiments surrogate values for $T_2$ and/or $T_1$ can be obtained and used (e.g., $T_2^*$ (the decay time constant from a free induction decay curve), LW, the linewidth (LW) of a peak from a Fourier transformed NMR spectra, or any other representation of the NMR data that permits inferences or estimates of the $T_2$ relaxation rate). The delay from pulse to data acquisition can range from about 1 to about 50 milliseconds after the start of pulse scheme that acquires the relaxation decay curve; about 16 to about 20 milliseconds after the start of the pulse scheme; or about 19 milliseconds after the start of the pulse scheme. In some embodiments, the signal is used in a raw form, without the use of chemical shifts and without converting data into the frequency domain by Fourier transform or other means. The method can also be performed by, at least, partially suppressing the water signal prior to the beginning of a sequence used to record relaxation time constants in the time domain, analyzing the exponentially decaying NMR signal in the time domain using single- or multi-exponential analysis, and comparing differences in the relaxation time constants for water within a single human subject, or between subjects, to assess normal and abnormal water $T_2$ and/or $T_1$ values (or surrogate values therefor) that are reflective of increased disease risk or active disease. In another aspect, the method comprises application of the disclosed method to a plurality of samples obtained from a plurality of subjects and developing a database of $T_2$ and/or $T_1$ values (or alternatively, surrogate values such as $T_2^*$ (the decay time constant from a free induction decay curve), or LW, the linewidth of a peak from a Fourier transformed NMR spectra, or any other representation of the NMR data that permits inferences or estimates of the $T_2$ relaxation rate) for water in said samples. The database can be used to provide a range of values for individuals having, or at risk of developing, a disorder such as insulin resistance, inflammation, dyslipidemia, oxidative stress and brain abnormalities (e.g., lower cognitive scores or mild cognitive impairment that often precedes Alzheimer's disease or Parkinson's disease).

In some embodiments, the database can provide further guidance in the development of $T_2$ and/or $T_1$ Health Score (based on $T_2$ and/or $T_1$ values). For example, plasma $T_2$ and/or $T_1$ Health Scores >800 are indicative of the lowest likelihood of metabolic abnormalities; $T_2$ and/or $T_1$ Health Score values of between 700-800 or 720 to 800 indicate a medium likelihood of metabolic abnormalities; and $T_2$ and/or $T_1$ Health Score values of <700 or <720 are indicative of the highest likelihood of metabolic abnormalities.

In another aspect, the invention is a diagnostic kit that includes a pulse time domain or frequency domain NMR instrument, a sample selected from the group consisting of serum and plasma, and a database of $T_2$ and/or $T_1$ data for water that correlates with a disorder such as insulin resistance, inflammation, dyslipidemia, oxidative stress and brain abnormalities (e.g., low cognitive scores or mild cognitive impairment).

The general principles of time domain pulse NMR are generally well understood and familiar to persons of ordinary skill in the art and need not be discussed in detail. In brief, however, a sample is positioned in an external magnetic field provided by a permanent magnet. This aligns the magnetic moments of the hydrogen atoms with (or against) the permanent magnetic field. Then, a radio frequency pulse is applied in a direction that provides a secondary (temporary) magnetic field perpendicular to the permanent magnetic field. This moves the magnetic moments of the hydrogen atoms away from their equilibrium state. The time duration of the pulse determines how far the magnetic moments move. The combined movement of many spins (many hydrogen atoms) generates a small but detectable oscillating magnetic field that in turn induces an alternating voltage that is measured as the NMR signal by a detection coil.

At the end of the pulse, the protons in the sample give up excess energy to their surroundings and relax back to the equilibrium state with respect to the permanent magnetic field. This relaxation takes a certain amount of time, so that the NMR signal remains detectable for a period of time that can range from several milliseconds to several seconds. Furthermore, the relaxing component of the NMR signal will be characteristic of individual mobility domains, which in turn, help identify the molecules involved in the motions and the rate of the motions. Samples can be scanned and the NMR signal acquired multiple times, such as between 1 and 256 times or up to 10 to 50 times.

In one embodiment, the hydrogen spin-spin relaxation rate constants (or time constants) are measured using a low-field bench-top time-domain NMR analyzer, and the relaxation rate constant for water is resolved through a single- or multi-exponential deconvolution algorithm. The analysis can be made directly on serum, plasma, whole blood or intact tissue. Because of the relative simplicity and low cost, this method has potential application to clinical testing for the detection of a disorder such as insulin resistance, inflammation, dyslipidemia, oxidative stress and brain abnormalities (e.g., low cognitive scores or mild cognitive impairment). Alternatively, the measurements can be made in conventional low or high-field spectrometers, magnetic resonance imagers (MRI) or a portable, wearable NMR device. In one embodiment, a tube containing a sample is placed into the bore of the magnet of a bench-top TD-NMR analyzer. Typically, the analyzer can be operated at 5, 10, 20, 40 or 60 MHz resonance frequency for hydrogen.

A Car-Purcell-Miniboom-Gill (CPMG) pulse sequence can, in some embodiments, be used to measure the exponential $T_2$ time-decay curve for water. This pulse sequence effectively eliminates chemical shifts and magnetic field inhomogeneity, permitting the measurement of $T_2$ values. Of course, any pulse sequence capable of measuring $T_2$ or surrogate measures of $T_2$ such as $T_2^*$ (the decay rate of a free induction decay signal), NMR peak linewidth (typically the half-height linewidth of a Fourier transformed NMR signal), or any other representation of the NMR data that permits inferences or approximation of the $T_2$ relaxation rate and, if necessary, partially suppressing the water signal can be used in the disclosed method. Although $T_2$ measurements can be linked with chemical shifts and measured in the frequency domain, the TD-NMR embodiment of this method measures $T_2$ in the time domain without chemical shifts. The resulting $T_2$ decay curve for human serum is typically multi-exponential. However, even though the curve is multi-exponential, a rough estimate of water $T_2$ may be obtained using a single exponential analysis. Thus, the individual exponential terms can be deconvoluted and resolved with the use of an inverse Laplacian transform. The mathematical calculation can be implemented using Xpfit, a public domain program, among other open-source or commercially available solutions. While the use of an inverse Laplace transform is exemplified in this application for the exponential analysis algorithm, any other suitable exponential analysis algorithm can be used for the analysis of the exponential data acquired by the practice of the disclosed methods. With respect to the exponential analysis of the acquired data, at least one exponential term is analyzed. In various embodiments, between one and 10 terms are analyzed. Other embodiments provide for the analysis of up to 6 terms or up to three exponential terms.

Plasma and serum water $T_2$ values from TD-NMR have been correlated with over 70 blood tests (Tables 2-6). Strong correlations exist between plasma water $T_2$, plasma viscosity and total serum protein concentration, particularly serum globulins (Table 1). Inflammatory markers also correlated with plasma water $T_2$. These include the inflammatory markers: C-reactive protein, white blood cell counts and neutrophil counts. Plasma water $T_2$ also correlated with the following markers of insulin resistance: insulin C-peptide, HOMA2-IR, triglycerides and $HbA_{1c}$.

Serum water $T_2$ values reveal a set of correlations similar to those of plasma. Serum water $T_2$ correlates with a number of LDL-related cholesterol markers. Serum water $T_2$ also shows significant correlations with serum protein, globulin and albumin concentrations as well as serum viscosity. Additionally, serum water $T_2$ also correlates with white blood cell counts, neutrophil counts and C-reactive protein (inflammatory markers). Thus, serum water $T_2$ values can be used to assess the risk or presence of disorders such as inflammation or dyslipidemia (lipid disorders in a subject).

The disclosed methods can also be coupled with treatments (under the supervision of a physician or appropriate licensed health care provider) for the disorders discussed herein for subjects identified to be at risk for the development of diabetes, coronary artery disease, Alzheimer's disease, etc. For example, subjects with evidence of inflammation can be treated with a variety of anti-inflammatory agents. Non-limiting examples of such agents include: non-steroidal anti-inflammatory agents such as ibuprofen, naproxen, aspirin, celecoxib, sulindac, oxaprozin, salsalate, diflunisal, piroxicam, indomethacin, etodolac, meloxicam, nambumetone, ketorolac tromethamine, and diclofenac; corticosteroids, such as beclomethasone, beclometasone, budesonide, flunisolide, fluticasone, triamcinolone, methylprednisolone, prednisolone or prednisone. For patients showing evidence of insulin resistance, the patients can be treated by altering diet, initiating a diabetic treatment, increasing exercise or otherwise modifying behavior so as to reduce the likelihood of developing diabetes arising from insulin resistance. For subjects showing evidence of a dyslipidemia, the subject can be treated with low dose aspirin and/or statins (such as atorvastatin, fluvastatin, lovastatin, pitavastatin, pravastatin, rosuvastatin or simvastatin), or another suitable lipid-lowering therapy.

Figure 5:
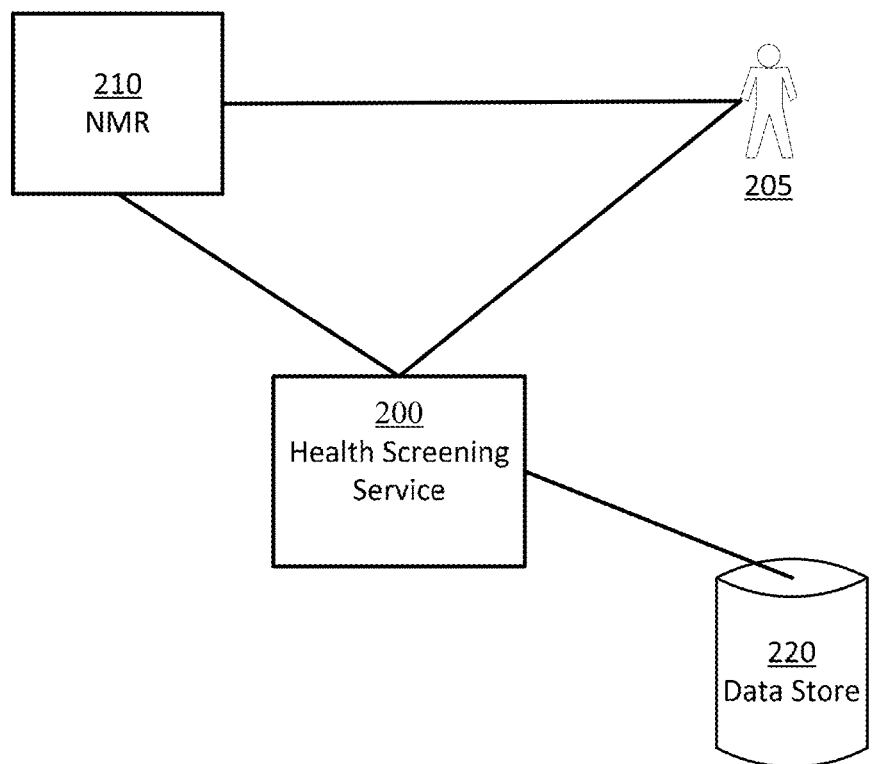
FIG. 5 illustrates an example system architecture in which an implementation of techniques for health screening using $T_1$ and/or $T_2$ values for water may be carried out.

FIG. 5 illustrates an example system architecture in which an implementation of techniques for health screening using $T_1$ and/or $T_2$ values for water may be carried out. In the example illustrated in FIG. 5, a health screening service 200 may receive information from an NMR 210, used to process a subject 205 sample. Health screening service 200 may output results, such as a health score or treatment information to subject 205.

A device appropriate for a health screening service 200 may be implemented as software or hardware (or a combination thereof) on a device which may be an instantiation of system 300. Such a device may be or include computing systems or devices such as a laptop, desktop, tablet, reader, mobile phone, wearable device, "Internet of things" device, and the like.

An NMR device 210 may be laboratory device (such as an NMR or MM instrument), bench-top device, or even a portable device. A portable NMR device 210 may be capable of being worn (e.g., wearable), connected to or adjacent to a subject's skin through a biosensor. In such cases the NMR device 210 may communicate with the health screening service over a wireless communications network, such as Bluetooth®.

Health screening service 200 may interact with a data store 220, which can store biomarkers and their associated $T_1$ and/or $T_2$ reference values and/or ranges for different sample types. Data store 220 may also store additional information, for example, treatment information and data sets derived from samples gathered from other subjects. All or part of data store 220 may be instantiated on the same system as health screening service, or may be instantiated on multiple systems, connected by a network.

Communications and interchanges of data between components in the environment may take place over a network (not shown). The network can include, but is not limited to, a cellular network (e.g., wireless phone), a point-to-point dial up connection, a satellite network, the Internet, a local area network (LAN), a wide area network (WAN), a Wi-Fi network, an ad hoc network, an intranet, an extranet, or a combination thereof. The network may include one or more connected networks (e.g., a multi-network environment) including public networks, such as the Internet, and/or private networks such as a secure enterprise private network.

Figure 6:
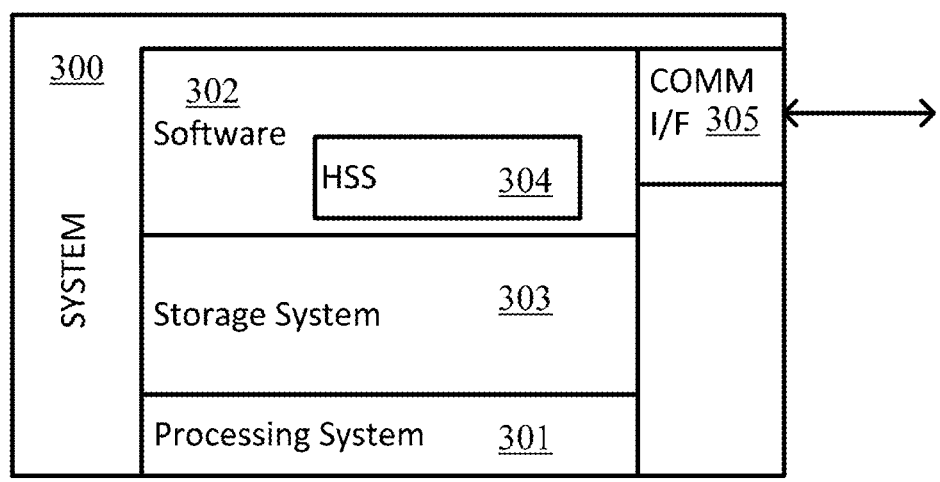
FIG. 6 shows a block diagram illustrating components of a computing device or system used in some implementations of an apparatus for health screening using $T_1$ and/or $T_2$ values for water.
Figure 7:
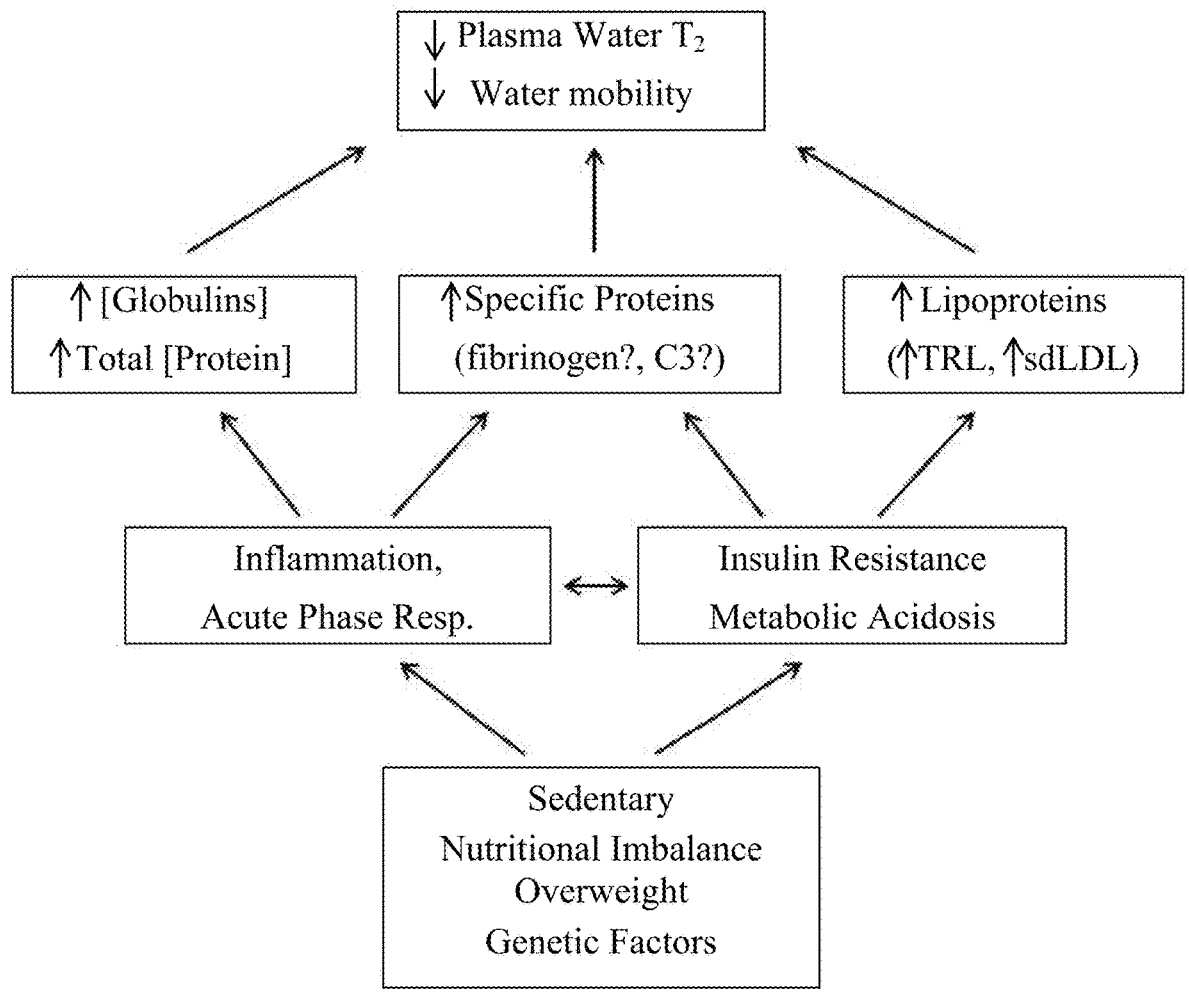
FIG. 7 presents a schematic overview of the proposed linkage between metabolic abnormalities, traditional clinical measures and plasma water $T_2$.

FIG. 6 shows a block diagram illustrating components of a computing device or system used in some implementations of an apparatus for health screening using $T_1$ and/or $T_2$ values for water. For example, any computing device operative to run a health screening service 200 or intermediate devices facilitating interaction between other devices in the environment may each be implemented as described with respect to system 300, which can itself include one or more computing devices. The system 300 can include one or more blade server devices, standalone server devices, personal computers, routers, hubs, switches, bridges, firewall devices, intrusion detection devices, mainframe computers, network-attached storage devices, and other types of computing devices. The hardware can be configured according to any suitable computer architectures such as a Symmetric Multi- Processing (SMP) architecture or a Non-Uniform Memory Access (NUMA) architecture.

The system 300 can include a processing system 301, which may include a processing device such as a central processing unit (CPU) or microprocessor and other circuitry that retrieves and executes software 302 from storage system 303. Processing system 301 may be implemented within a single processing device but may also be distributed across multiple processing devices or sub-systems that cooperate in executing program instructions.

Examples of processing system 301 include general purpose central processing units, application specific processors, and logic devices, as well as any other type of processing device, combinations, or variations thereof. The one or more processing devices may include multiprocessors or multi-core processors and may operate according to one or more suitable instruction sets including, but not limited to, a Reduced Instruction Set Computing (RISC) instruction set, a Complex Instruction Set Computing (CISC) instruction set, or a combination thereof. In certain embodiments, one or more digital signal processors (DSPs) may be included as part of the computer hardware of the system in place of or in addition to a general purpose CPU.

Storage system 303 may comprise any computer readable storage media readable by processing system 301 and capable of storing software 302 including health screening service 200 and/or data store 220. Storage system 303 may include volatile and nonvolatile, removable and non-removable media implemented in any method or technology for storage of information, such as computer readable instructions, data structures, program modules, or other data.

Examples of storage media include random access memory (RAM), read only memory (ROM), magnetic disks, optical disks, CDs, DVDs, flash memory, solid state memory, phase change memory, or any other suitable storage media. Certain implementations may involve either or both virtual memory and non-virtual memory. In no case do storage media consist of a propagated signal. In addition to storage media, in some implementations, storage system 303 may also include communication media over which software 302 may be communicated internally or externally.

Storage system 303 may be implemented as a single storage device but may also be implemented across multiple storage devices or sub-systems co-located or distributed relative to each other. Storage system 303 may include additional elements, such as a controller, capable of communicating with processing system 301.

Software 302 may be implemented in program instructions and among other functions may, when executed by system 300 in general or processing system 301 in particular, direct system 300 or processing system 301 to operate as described herein for enabling health screening with $T_2$ and/or $T_1$ values. Software 302 may provide program instructions 304 that implement a health screening service 200 or subcomponents thereof. Software 302 may implement on system 300 components, programs, agents, or layers that implement in machine-readable processing instructions the methods described herein as performed by health screening service 200 (as instructions 304).

Software 302 may also include additional processes, programs, or components, such as operating system software, database management software, or other application software. Software 302 may also include firmware or some other form of machine-readable processing instructions executable by processing system 301.

In general, software 302 may, when loaded into processing system 301 and executed, transform system 300 overall from a general-purpose computing system into a special-purpose computing system customized to facilitate health screening with $T_2$ and/or $T_1$ values. Indeed, encoding software 302 on storage system 303 may transform the physical structure of storage system 303. The specific transformation of the physical structure may depend on various factors in different implementations of this description. Examples of such factors may include, but are not limited to, the technology used to implement the storage media of storage system 303 and whether the computer-storage media are characterized as primary or secondary storage.

System 300 may represent any computing system on which software 302 may be staged and from where software 302 may be distributed, transported, downloaded, or otherwise provided to yet another computing system for deployment and execution, or yet additional distribution.

In embodiments where the system 300 includes multiple computing devices, one or more communications networks may be used to facilitate communication among the computing devices. For example, the one or more communications networks can include a local, wide area, or ad hoc network that facilitates communication among the computing devices. One or more direct communication links can be included between the computing devices. In addition, in some cases, the computing devices can be installed at geographically distributed locations. In other cases, the multiple computing devices can be installed at a single geographic location, such as a server farm or an office.

A communication interface 305 may be included, providing communication connections and devices that allow for communication between system 300 and other computing systems (not shown) over a communication network or collection of networks (not shown) or the air. Examples of connections and devices that together allow for inter-system communication may include network interface cards, antennas, power amplifiers, RF circuitry, transceivers, and other communication circuitry. The connections and devices may communicate over communication media to exchange communications with other computing systems or networks of systems, such as metal, glass, air, or any other suitable communication media. The aforementioned communication media, network, connections, and devices are well known and need not be discussed at length here.

It should be noted that many elements of system 300 may be included in a system-on-a-chip (SoC) device. These elements may include, but are not limited to, the processing system 301, a communications interface 305, and even elements of the storage system 303 and software 302.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules.

Materials and Methods

Subject recruitment. Human subject volunteers were recruited with informed consent into two protocols approved by the Institutional Review Board of the University of North Texas Health Science Center in Fort Worth (UNTHSC). One protocol recruited apparently healthy adult subjects from the student and staff population of UNTHSC, including some spouses and significant others. The second protocol recruited community members enrolled in the Health and Aging Brain Study at UNTHSC (8). Exclusion criteria for the current study included diabetes (HbA$_{1c}$>6.4), acute/chronic infection or illness (C-reactive protein >10), or not fasting for at least 12 hours. Characteristics of the human study group are detailed in Table 1.

Plasma and serum preparation. Fasting blood samples were drawn in the morning by a trained nurse or phlebotomist. For plasma preparation, blood was drawn into lavender-top tubes containing EDTA as the anticoagulant. For serum, blood was drawn into plain glass red-top tubes lacking any gel separator or clot activators (BD model 366441) in order to avoid potential interference of additives with TD-NMR or viscosity testing. Blood obtained for NMR LipoProfile analysis (LabCorp/LipoScience) was drawn into black-top tubes specialized for that purpose. Every effort was made to collect enough blood from each subject to perform all 70+ planned measurements. However, there were situations where the amount of blood collected from a given subject was not sufficient or samples were rejected by the testing lab. That variability accounts for the test-to-test differences in sample size (n) in the statistical analyses.

Blood sample analysis and banking. The plasma and serum samples were processed immediately after each blood draw. The samples were centrifuged to remove pelleted blood cells, followed by a second low speed spin of the supernatant to remove residual blood cells. The TD-NMR water $T_2$ measurements were performed five times on a sample of fresh plasma followed immediately by five repeats on fresh serum such that all water $T_2$ measurements were completed within ~2 hours after the blood draw. Likewise, viscosity was measured in house on fresh serum and plasma samples within a few hours of the blood draw using a VISCOLab3000 instrument as described elsewhere (9). Aliquots of fresh serum were sent on ice to Atherotech, Inc. for Vertical Autoprofile (VAP) advanced lipoprotein testing, as well as to determine LDL-P, hs-CRP, GGT, homocysteine, and Lp(a). Aliquots of plasma and serum were frozen at −80° C. prior to in-house analysis using assay kits: apolipoprotein E concentration (Abcam, Ab108813); ORAC anti-oxidant capacity (Cell Biolabs, STA-345), protein carbonyl content (Cell Biolabs STA-307), and HNE (Cell Biolabs, STA-838); and free fatty acids (BioAssay Systems, EFFA-100). All other testing of serum and plasma samples was performed by LabCorp, Quest Diagnostics and their affiliates including LipoScience (NMR LipoProfile) and OmegaQuant (Omega-3 Index). Plasma aliquots for amino acid analysis were frozen immediately after preparation and stored at −80° C. prior to shipment to Quest.

Samples for controlled experiments. All samples were prepared with phosphate-buffered saline, pH 7.4. Reagents obtained from Sigma-Aldrich included human serum albumin (Catalog No. A8763), human γ-globulin (G4386), uric acid (U2625), DL-lactic acid (69785), malondialdehyde tetrabutylammonium salt (63287) and glyceraldehyde (G5001). Reagents obtained from Fisher Scientific included adenosine-tri-phosphate (S25123), D-glucose (D15-500), urea (BP169-500) and cupric sulfate (S25285).

Benchtop Time-domain NMR Relaxometry. Measurements of $T_2$ and $T_1$ were performed at 37° C. using a Bruker mq20 Minispec benchtop time-domain NMR instrument equipped with a 10 mm variable temperature probe (Model H20-10-25-AVGX). The 10 mm NMR tube, which included a Wilmad coaxial insert, was filled to a sample height of 1 cm, corresponding to a sample volume of ~70 microliters.

The pulse sequence for $T_2$ measurement is illustrated in FIG. 1 of ref (10). In our experience, a critical factor in obtaining high quality TD-NMR data with aqueous samples is carefully tuning the delta delay to avoid radiation damping, particularly when 10 mm tubes are used without a coaxial insert. Radiation damping occurs when the additional magnetic field created by the intense oscillating water signal distorts the performance of CPMG pulse scheme (11). Radiation damping manifests itself by a non-random oscillatory artifact observed in the residuals of the fit after inverse Laplace transform. We determined empirically that a delta delay of $0.95*T_1$ (leading to a water signal that is ~23% of its full intensity) provides a level of suppression of the water sufficient to avoid radiation damping, while still maximizing the overall signal intensity of the water and the other lipid/protein peaks for analysis. Even after partial suppression, the intensity of the water signal was still sufficiently intense to measure water $T_2$ with high precision after only 8-16 scans. In this regard, the goal of water suppression in TD-NMR is different from that of frequency-domain NMR spectroscopy, as essentially complete suppression of the water is typically desired in the latter.

Radiation damping could also be eliminated by reducing the amount of sample in the probe. Use of a Wilmad coaxial insert reduced the sample volume down to ~70 microliters (from ~600 microliters). With the insert, it was no longer necessary to suppress the water signal.

Another unique aspect to this TD-NMR pulse scheme was the delayed acquisition of the data points, which began 19 ms after the beginning of the CPMG scheme. This strategy de-emphasizes the very fast processes at the beginning of the decay curve in order to emphasize the slower processes such as the water. This delayed acquisition scheme reduces the number of exponential terms, simplifying the inverse Laplace transform calculation. If attempts are made to fit the data using too many exponential terms, the calculation can become unstable, as it becomes a mathematically ill-posed problem. Such overfitting is evidenced by poor run-to-run precision, which was not observed using the current protocol.

For quantification of serum and plasma water $T_2$ values, each raw CPMG decay curve was analyzed using an inverse Laplace transform as implemented in the discrete components analysis of XPFit (see Worldwide Website: softscientific.com/science/xpfit.html). An important consideration for sample-to-sample comparisons is to restrain the number of exponential terms to a consistent number; the data obtained with 16 scans were fit to three terms. Less than three is not adequate to fit the data, as evidenced by poor residuals. Given the high signal-to-noise ratio of the water, it is not difficult to obtain stable fitting solutions for serum or plasma water $T_2$ data recorded with 16 scans. For illustrative purposes, the $T_2$ profile distributions shown in FIG. 1 were generated using CONTIN (s-provencher.com), even though the $T_2$ values were quantified using XPFit as described above. The water $T_2$ values from CONTIN and XPFit are essentially identical. XPFit has the advantage of being able to constrain the number of exponentials and employs a non-negative truncated single value decomposition algorithm, which stabilizes the calculation.

Statistical Analysis. The correlation, linear regression and statistical analyses were performed using GraphPad Prism v. 6.05 (GraphPad Software, Inc.) and JMP Pro v. 12.1.0 (SAS, Inc.). Some of the guiding principles for the statistical analyses were derived from the book by Motulsky (12). The null hypothesis states that there is no correlation between the variables being compared. The two-tailed p value defines the probability of observing a correlation as strong or stronger if the null hypothesis were true. For example, for r=−0.6 and p<0.01, there is less than 1% probability of observing a correlation this strong or stronger by random chance; thus, the null hypothesis is rejected. For each correlation that met p-value thresholds, we inspected the plot to ensure that the correlation was not heavily influenced by one or two outliers. Sample plots are provided in FIG. 1. Regression residuals were analyzed in GraphPad Prism using the simple strategy outlined in the web link within ref. (13).

Example 1

Unlike conventional frequency-domain NMR spectroscopy, benchtop time-domain NMR relaxometry is based on the exponential analysis of the raw time-domain signal to extract a distribution of relaxation time constants (10). This distribution is referred to as a $T_2$ profile, which superficially resembles a NMR spectrum, but has a different x-axis and a fundamentally different meaning. The $T_2$ profile is calculated using an inverse Laplace transform and represents the distribution of $T_2$ values consistent with the exponentially-decaying time-domain signal. An example of a $T_2$ profile for human serum is provided in FIG. 2B of ref (10). The water peak represents approximately 94% of the total intensity, and the remaining 6% is captured in 2-3 tiny peaks arising from the non-labile hydrogen atoms from blood lipids and proteins. An overlay of the water peak from 29 human subjects, displayed in FIG. 2C of ref (10), reveals the remarkably wide variation in serum water $T_2$ values among apparently healthy volunteers.

The characteristics of the current human subject group are presented in Table 1. Overall, this is an apparently healthy group of adult volunteers spanning a wide age range. The exclusion criteria were diabetes (HbA$_{1c}$≥6.5, fasting glucose ≥125 mg/dL or prior diagnosis) or acute/chronic illness (C-reactive protein >10 or history of recent or chronic illness). In all cases, the mean values for various diagnostic markers fell within the normal reference ranges, near the middle of those ranges. The range of values across the study group coincided well with the normal reference ranges, although specific values for a few individuals were outside of those ranges. With respect to glycemia, 46 of the 51 subjects had fasting glucose levels <100 mg/dL and the remaining 5 did not exceed 115.

The plasma and serum water $T_2$ values from TD-NMR showed considerable variation across the study population (Table 1). To identify the factors governing the variation, we measured over 70 diagnostic tests and blood biomarkers and correlated them with plasma and serum water $T_2$ values (Table 2). The statistically-significant bivariate correlation coefficients for plasma water $T_2$ are listed in Table 3, and examples of the corresponding scatterplots are shown in FIG. 1. The strongest correlations were observed between plasma water $T_2$ and fasting insulin or insulin C-peptide, as well as various indices derived from insulin, glucose and/or triglycerides (Table 3, (A)). In addition, a strong correlation was observed with total serum protein concentration, and to a lesser extent serum globulins and viscosity, but not serum albumin (Table 3, (B)). Moreover, strong correlations were observed with markers of inflammation (Table 3, (C)), especially C-reactive protein and white blood cell count. Finally, correlations were observed with a variety of cholesterol-rich lipoprotein markers (Table 3, (D)). Plasma water $T_2$ measurements did not correlate with body-mass index or age.

Serum water $T_2$ values revealed bivariate correlations similar to those of plasma, although the insulin-related variables had somewhat lower correlation coefficients.

The bivariate correlations led us to consider the factors that may contribute directly to the variation in plasma and serum water $T_2$, as well as those that may be indirectly linked through another variable or a network of variables. Human blood plasma and serum are complex mixtures containing hundreds of different proteins and lipoproteins as well as numerous small molecule metabolites. At first thought, de-convoluting these myriad variables would seem to be hopelessly complex. However, the ten most abundant proteins in plasma (albumin, IgG, transferrin, fibrinogen, IgA, alpha2-macroglobulin, IgM, alpha$_1$-antitrypsin, C3 complement and haptoglobin) account for over 90% of total protein mass and the top two, nearly 80% (14). So identifying the primary contributors to water $T_2$ may be feasible.

We used three approaches to tease apart some of these factors. The first approach utilized a principal components analysis to identify clusters of variables in this dataset that are most closely related. The second approach utilized regression residuals (13), eliminating the influence of one variable while examining the correlations of plasma water $T_2$ with the remaining ones. The third approach made use of multiple regression models to control for the effect of confounders and identify independent contributors to water $T_2$.

Table 4 lists the parameters associated with the best multiple regression models identified for plasma water $T_2$. These models contained 2-5 terms. The most prominent and independent contributors to plasma water $T_2$ were insulin c-peptide, total serum protein and white blood cell count, with smaller contributions from HbA$_{1c}$ and total cholesterol.

Figure 2:
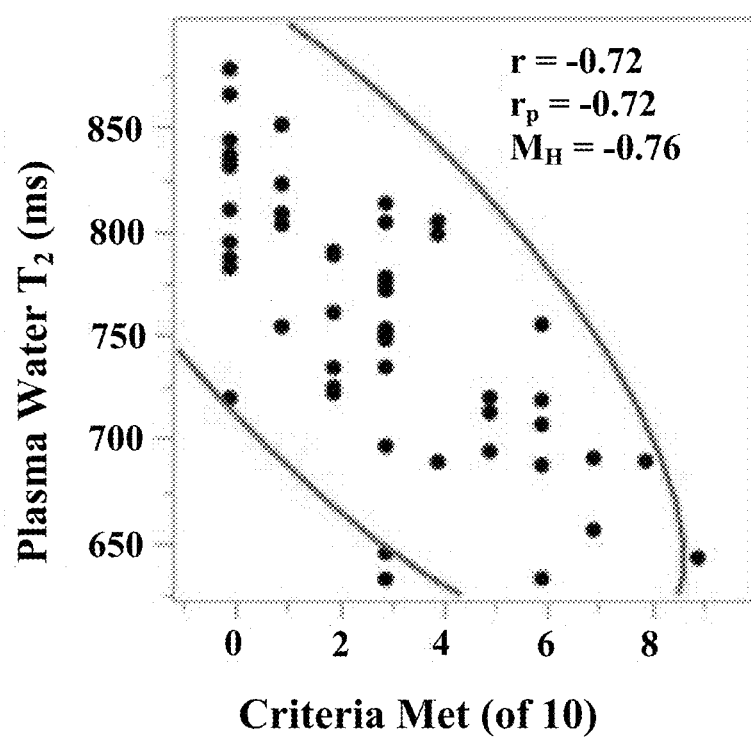
FIG. 2 plots the correlation between plasma water $T_2$ and the number of early insulin resistance measures that were positive in each subject. Each black circle represents an individual human subject enrolled in this study. Values are enclosed in the density ellipse calculated from the bivariate normal distribution fit to the X and Y variables at the 95% confidence level. The criteria represented along the x-axis are defined in Table 4. The values in the upper right corner are the Pearson, Spearman and Huber M-value coefficients for this correlation.

Table 5 uses a case-control format to compare the mean plasma $T_2$ values for different measures of hyperinsulinemia, dyslipidemia, inflammation and acid-base abnormalities. In all cases, the differences in the means were statistically significant. The differences were greatest with combinations of two or three metabolic conditions associated with early insulin resistance syndrome. FIG. 2 shows the progressive decrease and strong inverse correlation between plasma water $T_2$ values and the number of criteria met. The criteria refer to the measures listed in Table 5.

Figure 3:
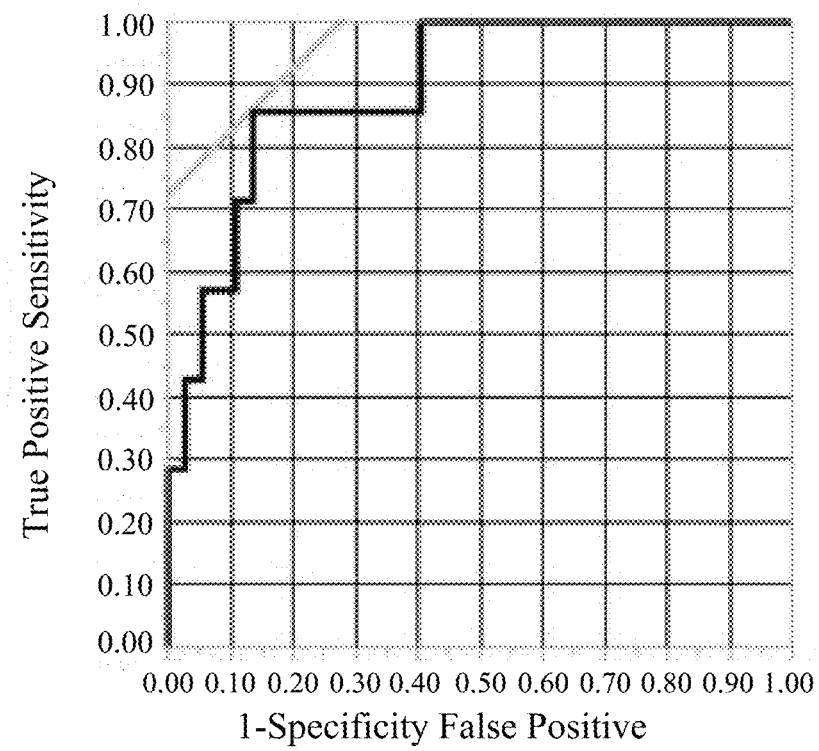
FIG. 3 shows receiver operator characteristic (ROC) curves that quantify and compare the ability of different tests to diagnose insulin resistance, as defined by the McAuley Index. top panel: plasma water $T_2$; middle panel: fasting glucose; bottom panel: HbA1c.
Figure 3:
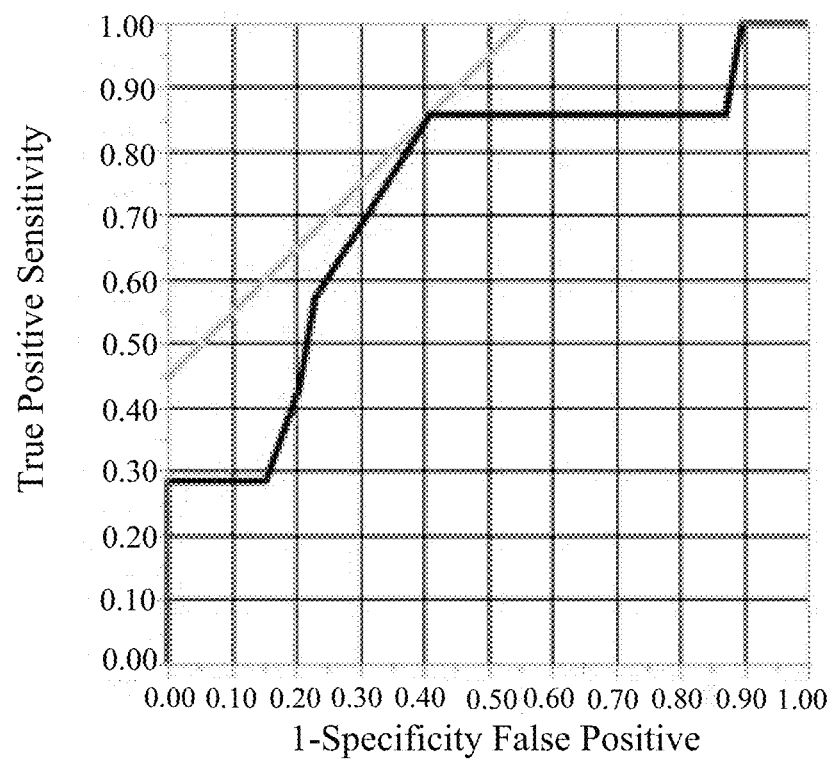
Figure 3:
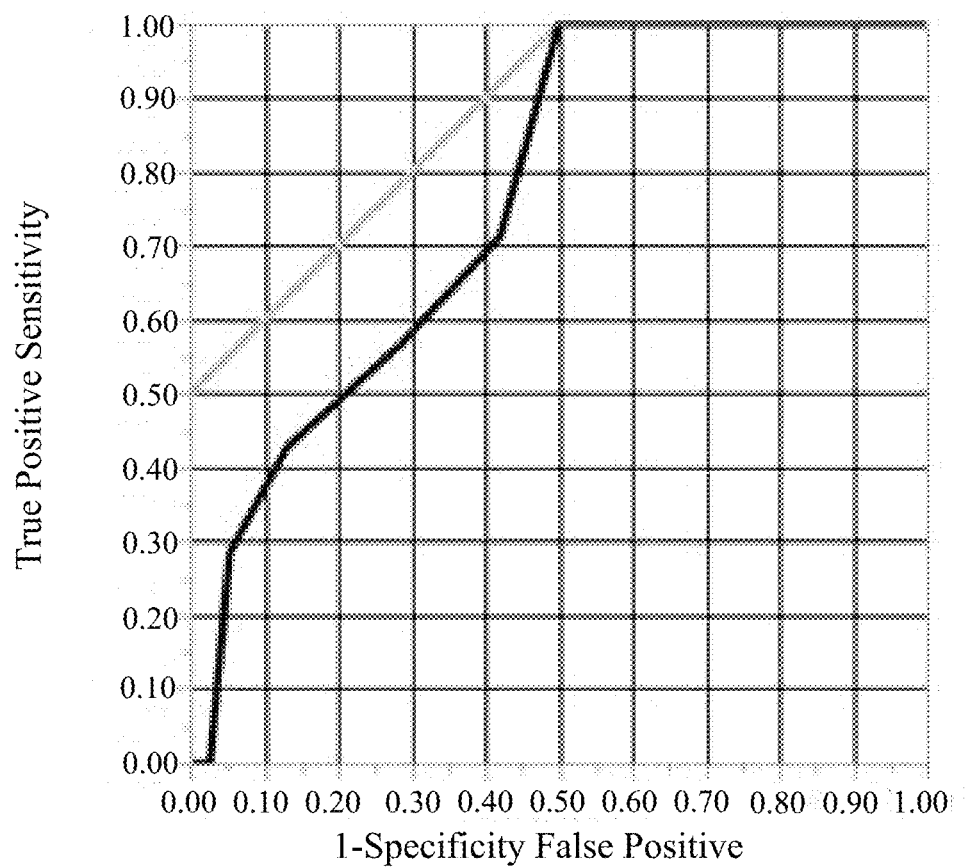
Figure 4:
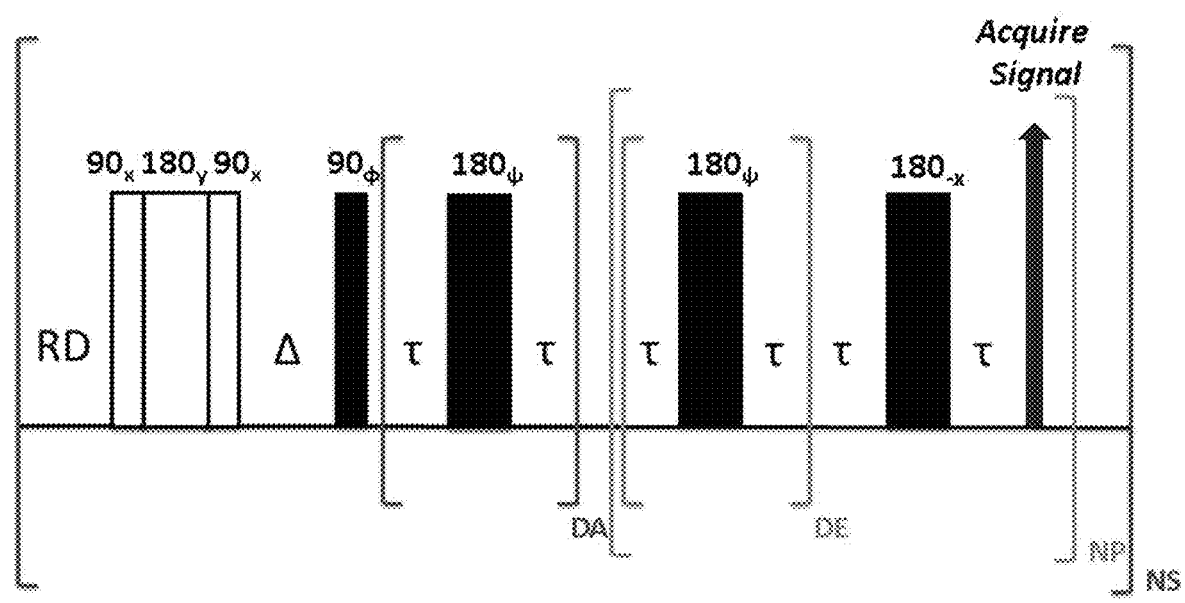
FIG. 4. Modified Carr-Purcell-Meiboom-Gill (CPMG) pulse sequence for measuring water $T_2$ in human serum or plasma using benchtop time-domain NMR. In contrast to NMR spectroscopy, the time points for the exponential decay curve are acquired directly during the CPMG pulse scheme, during the middle of the τ delay between successive 180° pulses, as designated by the arrow. For the current study, the first 180° pulse and A delay were added prior to the CPMG scheme to achieve partial water suppression and eliminate radiation damping. The Δ delay was tuned to 0.95*$T_1$ for each sample, which corresponds to suppression of the water to 23% of its full intensity. The τ delay was kept short (0.19 ms) to eliminate any possible impact of translational diffusion on $T_2$ in an inhomogeneous $B_o$ field. For all experiments, RD was set to 5*$T_1$, which corresponds to ~8 sec for serum or plasma; DE=5, NP=5600 and NS=16. The total experiment time was 6.4 minutes. Analysis of the resulting exponential decay curves is discussed in Materials and Methods. Abbreviations: RD, relaxation delay; DE, dummy echoes; NP, number of decay points acquired; NS, number of scans.

Table 6 lists the parameters obtained from receiver operator characteristic (ROC) curves, which quantify the relative ability of different biomarkers to diagnose insulin resistance, as defined by the McAuley Index. Sample ROC curves are shown in FIG. 3. The best curves stay closest to the left vertical and top axes, giving the largest value of area under the curve. Plasma water $T_2$ displayed the highest AUC and the best combination of sensitivity and specificity—superior to fasting glucose and hemoglobin A$_{1c}$, the tools widely used for diabetes screening and risk assessment.

These result of this study reveal, for the first time, the strong relationship between plasma water $T_2$ and components of the early insulin resistance syndrome. They demonstrate that plasma water $T_2$ is a sensitive and specific biomarker for insulin resistance—superior to glucose and hemoglobin A1c—and show the promise for plasma water $T_2$ to become a new diagnostic test for insulin resistance and for diabetes screening and risk assessment. Finally, the current results indicate the potential for using plasma water $T_2$ for routine health monitoring.

Lower values of water $T_2$ in serum and plasma are indicative of increasing degrees of metabolic dysfunction, even in apparently healthy human subjects. The unique value of this approach is that health status with respect to insulin resistance, low-grade inflammation, dyslipidemia and acid-base abnormalities can be assessed simultaneously in one measurement without having to order a panel of clinical lab tests or biomarkers. One could envision the development of a $T_2$ Health Score, a practical screening tool for the early identification of hidden abnormalities in healthy subjects, or for monitoring the effects of exercise or changes in diet.

Early detection and correction of subclinical abnormalities in healthy individuals could prevent the progression to serious diseases like diabetes, coronary artery disease, and possibly Alzheimer's disease. These disorders account for much of the morbidity and mortality in modern societies. Effective screening tools that can be implemented practically, inexpensively and broadly across the population will have a place in P4 medicine: personal, predictive, preventative and participatory (7).

Although this study focused on the analysis of blood plasma and serum, it is conceivable that similar information could be extracted from whole blood, after correcting for hematocrit. Conversely, information could be gleaned about blood cells after correcting for plasma protein levels. Given the intensity of the water NMR signal, it should be feasible to monitor the mobility of water in blood from outside of the body—without drawing blood—using a TD-NMR-enabled finger device, earlobe clip or a wristwatch-like device linked to a smart phone. This concept is not far-fetched, as compact, portable NMR devices are already in use in the industry.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Characteristics of the Human Study Group, n = 51 (insulin sensitivity and glucose tolerance ([A]), protein concentration and viscosity ([B]), inflammation ([C]), and cholesterol metabolism ([D]))

| Parameter | Mean ± SD | Range | Reference Values[1] |
|---|---|---|---|
| Age | 40 ± 16 | 23-80 | n/a |
| Gender | n/a | 24 female 27 male | n/a |
| Body-Mass Index ($kg/m^2$) | 26.4 ± 5.2 | 18.2-45.1 | <25 normal weight 25-30 overweight ≥30 obese |
| Plasma $T_2$ (ms) | 758.6 ± 65.1 | 633-878 | n.d |
| Serum $T_2$ (ms) | 814.6 ± 58.0 | 692-927 | n.d. |
| Total serum protein (g/dL)[B] | 7.1 ± 0.4 | 6.2-7.9 | 6.1-8.1 |
| Serum albumin (g/dL)[B] | 4.5 ± 0.3 | 3.6-5.0 | 3.6-5.1 |
| Serum globulins (g/dL)[B] | 2.7 ± 0.4 | 1.8-3.3 | 1.9-3.7 |
| WBC count(x $10^3$/μL)[C] | 6.5 ± 1.6 | 3.9-11.2 | 3.8-10.8 |
| Neutrophil count (x $10^3$/μL)[C] | 3.6 ± 1.3 | 1.8-7.3 | 1.5-7.8 |
| hs-CRP (mg/L)[C] | 2.5 ± 2.3 | 0.1-9.4 | <3.0 (low-to-average CV risk) 3.1-10.0 (high CV risk) >10.0 (infection/inflammation) |
| Glucose (mg/dL)[A] | 91.1 ± 7.6 | 78-115 | <100 non-diabetic 100-125 (pre-diabetic) |
| $HbA_{1c}$ (%)[A] | 5.5 ± 0.3 | 4.9-6.2 | <5.7 (non-diabetic) 5.7-6.4 (pre-diabetic) |
| Insulin C-peptide (ng/mL)[A] | 2.1 ± 0.9 | 0.9-5.1 | 0.8-3.9 (>2.85, IR) |
| Insulin (μU/mL)[A] | 9.3 ± 6.3 | 2.2-40.1 | 2.0-9.6 (>12.2, IR) |
| Triglycerides (mg/dL)[A] | 112 ± 59 | 42-321 | <150 |
| Total cholesterol (mg/dL)[D] | 189 ± 39 | 111-291 | <200 |
| HDL-C (mg/dL)[D] | 56 ± 12 | 32-85 | ≥40(male); ≥50 (female) |
| LDL-C (mg/dL)[D] | 111 ± 35 | 42-191 | <130 |
| Sodium (mmoles/L) | 140 ± 3 | 131-146 | 135-146 |
| Total $CO_2$, serum (mmoles/L) | 24 ± 3 | 16-29 | 19-30 |

[1]Reference values from Quest Diagnostics and Atherotech.

TABLE 2

Biomarkers Measured in this Study
TD-NMR Markers: plasma water $T_2$, $T_{2sa}$, $T_{2sp}$, $T_{2c}$; serum water $T_2$, $T_{2sa}$, $T_{2sp}$, $T_{2c}$ (insulin sensitivity and glucose tolerance ([A]), protein concentration and viscosity ([B]), inflammation ([C]), and cholesterol metabolism ([D]))

| Category | Statistical Correlation with $T_2$[†] | Did not correlate with $T_2$[†] |
|---|---|---|
| Protein, viscosity liver function markers[B] | total serum protein, serum albumin, serum globulins (calc), serum viscosity, plasma viscosity | α1-antitrypsin, AST, ALT, GGT |
| Inflammation, blood cell abd oxidative stress markers[C] | hs-CRP, WBC, neutrophils, monocytes, eosinophils, basophils, platelets, RDW, anion gap corrected for albumin concentration, TNFα*, sICAM*, I-309*, factor VII* | RBC, hematocrit, hemoglobin, MCV, MCH, MCHC, lymphocytes, HNE, ORAC antioxidant capacity |
| Cholesterol/lipid markers[D] | Total cholesterol, HDL-C, non-HDL-C, LDL-C, LDL-P, LDL size, small LDL-P, HDL-P, VLDL-C, remnant-C, apoB, DHA, omega-3 index | Lp(a), EPA, AA, apoAI phospholipids, apoE |
| Insulin resistance & diabetes markers[A] | insulin, insulin C-peptide, $HbA_{1c}$, HOMA2-IR, -% B, -% S, triglycerides IR Score (LipoScience) | glucose, free fatty acids, body-mass index |
| Electrolyte markers | chloride, bicarbonate, anion gap | sodium, potassium, calcium |
| Kidney function markers | blood urea nitrogen (BUN)*, estimated glomerular filtration rate (eGFR)* | creatinine |
| Thyroid function markers | thyroid stimulating hormone (TSH) | free T4 |

[†]In this table, a correlation si defined as one where $p < 0.05$ for at least two of the three following: Pearson, Spearman, or M-value correlation coefficients.
The individual coefficients and statistics are provided in Table 3.

TABLE 3

Bivariate correlation coefficients for plasma water $T_2$ with markers of insulin sensitivity and glucose tolerance ([A]), protein concentration and viscosity ([B]), inflammation ([C]), and cholesterol metabolism ([D]).

| Biomarker[1] | N | r (Pearson) | ρ (Spearman) | M-estimator (Huber) |
|---|---|---|---|---|
| Insulin C-peptide[2,A] | 50 | −0.67**** | −0.65**** | −0.70**** |
| Insulin[2,A] | 50 | −0.63**** | −0.59**** | −0.64**** |
| McAuley Index[A] | 50 | +0.64**** | +0.66**** | +0.66**** |
| HOMA-IR[2,3,A] | 50 | −0.67**** | −0.66**** | −0.71**** |
| QUICKI[A] | 50 | +0.64**** | +0.60**** | +0.68**** |
| FIRI[2,A] | 50 | −0.64**** | −0.59**** | −0.67**** |
| Glucose/Insulin Ratio[2,A] | 50 | +0.61**** | +0.58**** | +0.58**** |
| Glucose[2,A] | 50 | −0.37** | −0.40** | −0.43** |
| $HbA_{1C}$[A] | 49 | −0.52*** | −0.55*** | −0.59**** |
| TG[2,A] | 50 | −0.49*** | −0.51*** | −0.52*** |
| TG/HDL Ratio[A] | 50 | −0.44** | −0.43** | −0.42*** |
| Total Protein, Serum[B] | 49 | −0.57**** | −0.57**** | −0.60**** |
| Serum Globulins[B] | 49 | −0.44** | −0.44** | −0.45** |
| Serum Viscosity[2,B] | 46 | −0.41** | −0.44** | −0.52*** |
| C-reactive Protein[C] | 49 | −0.50*** | −0.49*** | −0.52*** |
| WBC Count[2,C] | 49 | −0.51*** | −0.51*** | −0.54**** |
| Neutrophil Count[2,C] | 49 | −0.46*** | −0.42** | −0.40** |
| Eosinophil Count[2,C] | 48 | −0.35* | −0.35* | −0.34* |
| Platelet Count[2,C] | 49 | −0.34* | −0.34* | −0.43** |
| LDL-C[2,D] | 49 | −0.42** | −0.44** | −0.39** |
| non-HDL-C[2,D] | 49 | −0.46*** | −0.47*** | −0.43** |
| VLDL-C[2,D] | 49 | −0.41** | −0.42** | −0.48** |
| IDL-C[2,D] | 49 | −0.31* | −0.34* | −0.33* |
| Remnant-C[2,D] | 49 | −0.35* | −0.40** | −0.40** |
| LDL-C/HDL-C Ratio[2,D] | 49 | −0.43** | −0.46*** | −0.54**** |
| Total C[2,D] | 49 | −0.40** | −0.43** | −0.39** |
| ApoB[2,D] | 49 | −0.47*** | −0.50*** | −0.48*** |
| ApoB/ApoAI[2,D] | 49 | −0.44** | −0.51*** | −0.58**** |
| LDL-p[D] | 48 | −0.47*** | −0.49*** | −0.46*** |

*$p < 0.05$; $p < 0.01$; *$p < 0.001$; ****$p < 0.0001$
[1]All biomarkers were measured following a 12-hour overnight fast.
[2]Variable was natural-log transformed in order to meet the condition of a normal (Gaussian) distribution.
[3]Calculated using fasting glucose and fasting insulin c-peptide as input.

TABLE 4

Single and Multiple Regression Models for Plasma Water $T_2$

| Model | Adjusted $R^2$ | Predictor Variables | Coefficients | p values |
|---|---|---|---|---|
| 1 | 0.42 | ln insulin c-peptide | −92.3 ± 15.3 | <0.0001**** |
|   |   | y-intercept | 817.5 ± 12.3 | <0.0001**** |
| 2 | 0.57 | ln insulin c-peptide | −72.9 ± 14.0 | <0.0001**** |
|   |   | total serum protein | −73.8 ± 16.0 | <0.0001**** |
|   |   | y-intercept | 1333 ± 113 | <0.0001**** |
| 3 | 0.64 | ln insulin c-peptide | −71.7 ± 12.9 | <0.0001**** |
|   |   | total serum protein | −64.1 ± 15.3 | <0.0001**** |
|   |   | ln WBC count | −76.3 ± 24.5 | 0.0033** |
|   |   | y-intercept | 1404 ± 107 | <0.0001**** |
| 4 | 0.67 | ln insulin c-peptide | −58.6 ± 13.4 | <0.0001**** |
|   |   | total serum protein | −62.3 ± 14.6 | <0.0001**** |
|   |   | ln neutrophil count | −47.4 ± 16.1 | 0.0001*** |
|   |   | $HbA_{1c}$ | −45.8 ± 18.6 | 0.0182* |
|   |   | y-intercept | 1882 ± 171 | <0.0001**** |
| 5 | 0.69 | ln insulin c-peptide | −48.8 ± 13.7 | 0.0010** |
|   |   | total serum protein | −60.9 ± 14.1 | <0.0001**** |
|   |   | ln neutrophil count | −45.9 ± 15.6 | 0.0052** |
|   |   | $HbA_{1c}$ | −46.7 ± 18.0 | 0.0130* |
|   |   | ln total cholesterol | −50.6 ± 24.6 | 0.0459* |
|   |   | y-intercept | 2124 ± 202 | <0.0001**** |

TABLE 5

Mean plasma water $T_2$ values for conditions and measures associated with early insulin resistance syndrome

| Conditions and Measures | Cutoff Value | Mean Plasma $T_2$ Values (ms) | | | p value[1] |
|---|---|---|---|---|---|
| | | No | Yes | Diff | |
| I. Hyperinsulinemia | any of 2 below | 773.7 | 707.6 | 66.1 | 0.0008*** |
| high fasting insulin | ≥12.2 µIU/mL[2] | 749.9 | 675.3 | 74.5 | 0.0063** |
| high insulin C-peptide | ≥2.85 mg/mL[3] | 746.3 | 666.2 | 80.1 | 0.0203* |
| II. Dyslipidemia | any of 3 below | 785.2 | 720.5 | 64.7 | 0.0008*** |
| high fasting TG | ≥132 mg/dL[2] | 772.9 | 714.4 | 58.5 | 0.0026** |
| small, dense LDL | pattern B or AB | 770.5 | 716.5 | 54.0 | 0.0071** |
| high LDL-p | ≥1468 nmoles/L[4] | 767.9 | 719.9 | 48.0 | 0.0210* |
| III. Inflammation | any of 3 below | 791.1 | 733.6 | 58.1 | 0.0011** |
| high C-reactive protein | ≥3.0 mg/L[5] | 774.1 | 723.4 | 50.7 | 0.0072** |
| high neutrophil count | ≥4200 cells/µL4 | 770.3 | 717.0 | 53.3 | 0.0080** |
| high serum globulins | >2.9 g/dL[4] | 774.3 | 727.4 | 46.9 | 0.0101* |
| IV. Acid-base abnormalities | any of 2 below | 778.2 | 721.9 | 56.3 | 0.0010** |
| low serum $CO_2$ | ≤22 meq/L | 769.2 | 719.3 | 49.9 | 0.0077** |
| high anion gap | ≥19.8 meq/L | 768.4 | 724.2 | 44.2 | 0.0212* |
| V. 2 or more conditions | see above | 798.9 | 721.3 | 77.6 | <0.0001**** |
| VI. 3 or more conditions | see above | 778.8 | 699.5 | 79.3 | <0.0001**** |
| VII. Hyperinsulinemia plus 1 or 2 more conditions | see above | 775.0 | 698.0 | 77.0 | <0.0001**** |

[1]Unpaired t-test for data sets with confirmed equal variances.
[2]As defined by McAuley et al. (ref).
[3]Determined by linear regression of fasting insulin C-peptide vs. fasting insulin, interpolating the C-peptide value corresponding to an insulin of 12.2 µIU/mL.
[4]Defined as upper quartile of subjects in this study.
[5]Defined as lower quartile of subjects in this study.

TABLE 6

Sensitivity, specificity and area-under-the-curve (AUC) parameters indicating the ability of various measures to diagnose insulin resistance (as defined by the McAuley Index) in normoglycemic subjects, n = 46.[1]

| Measure | AUC | Sensitivity | Specificity | Cutoff Value for IR |
|---|---|---|---|---|
| Plasma water $T_2$ | 0.90 | 86% | 86% | ≤718.8 ms |
| Glucose | 0.73 | 86% | 59% | ≥90.9 mg/dL |
| Glucose | 0.73 | 14% | 100% | ≥100 mg/dL[2] |
| $HbA_{1c}$ | 0.76 | 100% | 50% | ≥5.5% |
| $HbA_{1c}$ | 0.76 | 57% | 71% | ≥5.7%[2] |
| LDL-p | 0.87 | 100% | 69% | ≥1307 nmol/L |
| hs-CRP | 0.67 | 83% | 59% | ≥1.6 mg/L |
| Neutrophil count | 0.62 | 86% | 53% | ≥3498 cells/µL |
| Serum globulins | 0.70 | 100% | 42% | ≥2.6 g/dL |
| Serum total $CO_2$ | 0.82 | 86% | 70% | ≤23 mmol/L |
| Anion gap, corrected | 0.62 | 57% | 86% | ≥21 mmol/L |

[1]Parameters were derived from the receiver operator characteristic curves shown in FIG. 3.
Normoglycemic is defined as fasting glucose <100 mg/dL.
[2]American Diabetes Association criteria for prediabetes Abbreviations AA: arachidonic acid
ALT: alanine aminotransferase
AST: aspartate aminotransferase
BMI: body-mass index
BUN: blood urea nitrogen
CPMG: Carr-Purcell-Meiboom-Gill NMR pulse sequence to measure $T_2$
DHA: Docosahexaenoic Acid
EDTA: ethylene-diamine-tetra-acetic-acid
eGFR: estimated glomerular filtration rate
EPA: eicosapentaenoic Acid
GGT: gamma glutamyl transpeptidase
HABS: Health & Aging Brain Study at the UNT Health Science Center, Fort Worth
HABLE: Health and Aging Brains in Latino Elders, a sub-study of HABS
$HbA_{1C}$: glycated hemoglobin
HDL-C: high-density lipoprotein cholesterol concentration
HDL-P: high-density lipoprotein particle number concentration
HNE: 4-hydroxynonenal
HOMA2-% B: homeostatic model assessment version 2, % beta cell function
HOMA2-% S: homeostatic model assessment version 2, % insulin sensitivity
HOMA2-IR: homeostatic model assessment version 2, insulin resistance index (see Worldwide website: dtu.ox.ac.uk/homacalculator for HOMA2 definitions)
hs-CRP: high-sensitivity C-reactive protein
I-309: member of the CC subfamily of chemokines
IR Score: insulin resistance score (from NMR LipoProfile, LipoScience)
LDL-C: low density lipoprotein cholesterol concentration
LDL-P: low density lipoprotein particle number concentration
Lp(a): lipoprotein (a) cholesterol concentration
MCH: mean corpuscular hemoglobin
MCHC: mean corpuscular hemoglobin concentration
MCV: mean corpuscular volume
MDA: malondialdehyde
NMR, nuclear magnetic resonance
$T_{2a}$: regression residuals from a linear fit of plasma or serum water $T_2$ vs. serum albumin
$T_{2c}$: regression residuals from a linear fit of plasma or serum water $T_2$ vs. serum cholesterol $T_{2g}$: regression residuals from a linear fit of plasma or serum water $T_2$ vs. serum globulins (globulins=total serum protein−serum albumin)

$T_{2p}$: regression residuals from a linear fit of plasma or serum water $T_2$ vs. total serum protein $T_{2v}$: regression residuals from a linear fit of plasma or serum water $T_2$ vs. viscosity r: Pearson correlation coefficient $r_S$: Spearman correlation coefficient, non-parametric $R^2$: square of the Pearson correlation coefficient RDW: red cell distribution width Remnant-C: remnant lipoprotein particle cholesterol concentration sICAM: soluble intercellular adhesion molecule TD-NMR: time-domain nuclear magnetic resonance TG: serum triglyceride concentration TNFα: tumor necrosis factor alpha TSH: thyroid stimulating hormone

[UA]: unmeasured anion concentration, in meq/L

[UC]: unmeasured cation concentration, in meq/L

VAP: Vertical AutoProfile test, Atherotech

VLDL-C: very low density lipoprotein cholesterol concentration

WBC: white blood cells

REFERENCES

1. Mitchell, J.; Gladden, L. F.; Chandrasekera, T. C.; Fordham, E. J. Low-field permanent magnets for industrial process and quality control. *Prog Nucl Magn Reson Spectrosc* 2014, 76, 1-60.
2. Savaryn, J. P.; Catherman, A. D.; Thomas, P. M.; Abecassis, M. M.; Kelleher, N. L. The emergence of top-down proteomics in clinical research. *Genome Med.* 2013, 5, 53.
3. Apweiler, R.; Aslanidis, C.; Deufel, T.; Gerstner, A.; Hansen, J.; Hochstrasser, D.; Kellner, R.; Kubicek, M.; Lottspeich, F.; Maser, E.; Mewes, H. W.; Meyer, H. E.; Mullner, S.; Mutter, W.; Neumaier, M.; Nollau, P.; Nothwang, H. G.; Ponten, F.; Radbruch, A.; Reinert, K.; Rothe, G.; Stockinger, H.; Tarnok, A.; Taussig, M. J.; Thiel, A.; Thiery, J.; Ueffing, M.; Valet, G.; Vandekerckhove, J.; Verhuven, W.; Wagener, C.; Wagner, O.; Schmitz, G. Approaching clinical proteomics: current state and future fields of application in fluid proteomics. *Clin. Chem. Lab. Med.* 2009, 47, 724-744.
4. This is not a reference, but instead an explanatory note for where "(4)" appears in the specification. Although the current study emphasizes $T_2$, we also measured water $T_1$ (spin-lattice relaxation times) for the blood serum and plasma samples from this study population. The findings for $T_1$ will be addressed elsewhere.
5. Hansson, G. K. Inflammation, atherosclerosis, and coronary artery disease. *N. Engl. J. Med.* 2005, 352, 1685-1695.
6. De Felice, F. G.; Ferreira, S. T. Inflammation, Defective Insulin Signaling, and Mitochondrial Dysfunction as Common Molecular Denominators Connecting Type 2 Diabetes to Alzheimer Disease. *Diabetes* 2014, 63, 2262-2272.
7. Flores, M.; Glusman, G.; Brogaard, K.; Price, N. D.; Hood, L. P4 medicine: how systems medicine will transform the healthcare sector and society. *Per Med.* 2013, 10, 565-576.
8. O'Bryant, S. E.; Johnson, L.; Reisch, J.; Edwards, M.; Hall, J.; Barber, R.; Devous M D, S.; Royall, D.; Singh, M. Risk factors for mild cognitive impairment among Mexican Americans. *Alzheimers Dement.* 2013, 9, 622-631. el.
9. Robinson, M. D.; Cistola, D. P. Nanofluidity of Fatty Acid Hydrocarbon Chains As Monitored by Benchtop Time-Domain Nuclear Magnetic Resonance. *Biochemistry* 2014, 53, 7515-7522.
10. Cistola, D. P.; Robinson, M. D. Compact NMR Relaxometry of Human Blood and Blood Components. *Trends in Analytical Chemistry* 2016, in press.
11. Freeman, R. *A Handbook of Nuclear Magnetic Resonance*; Longman Group: United Kingdom, 1997.
12. Motulsky, H. *Intuitive Biostatistics: A Nonmathematical Guide to Statistical Thinking*; Oxford University Press: New York, 2010.
13. Klingenberg, C. P. Morphol: an integrated software package for geometric morphometrics (see also Worldwide website: flywings.org.uk/MorphoJ_guide/frameset.htm?covariation/regression.htm). *Mol. Ecol. Resour.* 2011, 11, 353-357.
14. Lundblad, R. Considerations for the Use of Blood Plasma and Serum for Proteomic Analysis. *The Internet Journal of Genomics and Proteomics* 2003, 1(2).

We claim:

1. A method for determining metabolic health of a subject, the method comprising:

acquiring data for a sample of the subject using a nuclear magnetic resonance (NMR) instrument or a magnetic resonance imaging (MRI) instrument tuned to measure a particular nucleus selected from $^1H$, $^2H$, $^3H$ or $^{17}O$, wherein the data comprises an NMR data set or spin relaxation curve for the sample;

analyzing the data to extract a water $T_2$ relaxation time of the sample;

determining the metabolic health of the subject based on the extracted water $T_2$ relaxation time, wherein the larger the water $T_2$ relaxation time, the better the metabolic health of the subject is determined to be; and upon extracting water $T_2$ relaxation time of less than 800 milliseconds (ms), treating the subject based on the extracted water $T_2$ relaxation time, wherein, upon a determination that the water $T_2$ relaxation time is less than a predetermined cutoff value, the treating of the subject comprises a referral to a physician for a workup and disease diagnosis, wherein the predetermined cutoff value is 720 ms or less, wherein, upon a determination that the water $T_2$ relaxation time is less than 800 ms but more than the predetermined cutoff value, the treating of the subject comprises an exercise program for the subject and a redetermination of the metabolic health of the subject after a predetermined period of time, and wherein the subject has a C-reactive protein level of 10 milligrams per liter (mg/L) or less, such that the subject has no clinical inflammation.

2. The method according to claim 1, wherein the analyzing of the data comprises the exponentially decaying or recovering NMR signal comprises transforming the data with an inverse Laplace transformation.

3. The method according to claim 1, wherein the analyzing of the data comprises performing a multi-exponential analysis on the data.

4. The method according to claim 1, wherein said sample is scanned multiple times.

5. The method according to claim 1, wherein the disease diagnosis comprises diagnosis of at least one of inflammation, insulin resistance, lipid abnormalities (dyslipidemia), oxidative stress, and brain abnormalities.

6. The method according to claim 1, wherein, upon a determination that the water $T_2$ relaxation time is less than 800 ms but more than the predetermined cutoff value, the treating of the subject further comprises an alteration of diet configured to improve insulin sensitivity and reduce the likelihood of the subject developing diabetes arising from insulin resistance.

7. The method according to claim 1, wherein the treating of the subject comprises prescribing an anti-oxidant.

8. The method according to claim 1, further comprising:
generating a $T_2$ metabolic health score based on the water $T_2$ relaxation time, wherein the $T_2$ metabolic health score is proportional to the water $T_2$ relaxation time.

9. The method according to claim 1, wherein the predetermined period of time is at least four weeks.

10. The method according to claim 1, wherein the sample is a plasma sample, a serum sample, a whole blood sample, or a tissue sample.

11. The method according to claim 10, wherein the obtaining of the data comprises performing data acquisition 1 millisecond to 50 milliseconds after a start of a pulse scheme that acquires a relaxation decay curve.

12. The method according to claim 1, wherein the analyzing of the data comprises partially suppressing a water signal with a 180-degree inversion pulse followed by a delay.

13. The method according to claim 12, wherein a time of the delay is tuned to eliminate radiation damping while maximizing water signal intensity.

14. The method according to claim 1, wherein the treating of the subject comprises treatment with one or more anti-inflammatory agents.

15. The method according to claim 14, wherein said anti-inflammatory agent is selected from ibuprofen, naproxen, aspirin, celecoxib, sulindac, oxaprozin, salsalate, diflunisal, piroxicam, indomethacin, etodolac, meloxicam, nambumetone, ketorolac tromethamine, or corticosteroids selected from as beclomethasone, beclometasone, budesonide, flunisolide, fluticasone, triamcinolone, methylprednisolone, prednisolone, or prednisone.

16. The method according to claim 1, wherein the treating of the subject comprises prescribing aspirin or a statin.

17. The method according to claim 16, wherein the statin is selected from atorvastatin, fluvastatin, lovastatin, pitavastatin, pravastatin, rosuvastatin, or simvastatin.

18. An apparatus for determining metabolic health of a subject, the apparatus comprising:
an instrument tuned to measure a particular nucleus selected from $^1H$, $^2H$, $^3H$ or $^{17}O$, wherein the instrument is a nuclear magnetic resonance (NMR) instrument or a magnetic resonance imaging (MRI) instrument;
a processor; and
a computer readable storage medium in operable communication with the processor and having instructions stored thereon that, when executed by the processor, perform the following steps:
acquire data for a sample of the subject using the instrument, wherein the data comprises an NMR data set or spin relaxation curve for the sample; analyze the data to extract a water $T_2$ relaxation time of the sample;
determine the metabolic health of the subject based on the extracted water $T_2$ relaxation time, wherein the larger the water $T_2$ relaxation time, the better the metabolic health of the subject is determined to be; and
upon extracting water $T_2$ relaxation time of less than 800 milliseconds (ms), recommend a treatment for the subject based on the extracted water $T_2$ relaxation time, wherein, upon a determination that the water $T_2$ relaxation time is less than a predetermined cutoff value, the treatment of the subject comprises a referral to a physician for a workup and disease diagnosis,
wherein the predetermined cutoff value is 720 ms or less,
wherein, if upon a determination that the water $T_2$ relaxation time is less than 800 ms but more than the predetermined cutoff value, the treatment of the subject comprises an exercise program for the subject and a redetermination of the metabolic health of the subject after a predetermined period of time, and
wherein the subject has a C-reactive protein level of 10 milligrams per liter (mg/L) or less, such that the subject has no clinical inflammation.

19. The apparatus according to claim 18, wherein the instructions when executed further perform the following step:
generate a $T_2$ metabolic health score based on the water $T_2$ relaxation time, wherein the $T_2$ metabolic health score is proportional to the water $T_2$ relaxation time.

20. The apparatus according to claim 18, wherein the analyzing of the data comprises performing a multi-exponential analysis on the data.

* * * * *